United States Patent
Cao et al.

(10) Patent No.: US 9,260,360 B2
(45) Date of Patent: Feb. 16, 2016

(54) MANUFACTURING PROCESS

(71) Applicant: ExxonMobil Chemical Patents Inc., Baytown, TX (US)

(72) Inventors: Chunshe Cao, Shanghai (CN); Jeffrey L. Andrews, Houston, TX (US); Michel Molinier, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 240 days.

(21) Appl. No.: 14/078,673

(22) Filed: Nov. 13, 2013

(65) Prior Publication Data

US 2014/0155668 A1 Jun. 5, 2014

Related U.S. Application Data

(60) Provisional application No. 61/733,656, filed on Dec. 5, 2012.

(51) Int. Cl.
*C07C 5/27* (2006.01)

(52) U.S. Cl.
CPC ............ *C07C 5/2737* (2013.01); *C07C 2529/78* (2013.01)

(58) Field of Classification Search
CPC ........................................................ C07C 5/27
USPC .................................................. 585/481, 904
See application file for complete search history.

(56) References Cited

U.S. PATENT DOCUMENTS

| 5,004,855 A | 4/1991 | Tada et al. |
| 5,516,956 A | 5/1996 | Abichandani et al. |
| 6,028,238 A | 2/2000 | Beck et al. |

OTHER PUBLICATIONS

Gellman et al., "*Studies of the Kinetics and Mechanisms of Ammonia Synthesis and Hydrodesulfurization on Metal Single-Crystal Surfaces,*" In Catalyst Characterization Science; Deviney M., et al.; ACS Symposium Series; American Chemical Society; Washington, DC, 1985.
Asscher et al., "*The Remarkable Surface Structure Sensitivity of the Ammonia Synthesis Over Rhenium Single Crystals,*" Surface Science Letters, Surface Science 143 (1984) L389-L392, North-Holland, Amsterdam, Elsevier Science Publishers B.V.
Hayashi et al., "*Ammonia synthesis over rhenium supported on mesoporous silica MCM-41,*" Microporous and Mesoporous Materials 146 (2011) pp. 184-189.
Kojima et al., "*Cesium-promoted rhenium catalysts supported on alumina for ammonia synthesis,*" Science Direct, Applied Catalysis A: General 246 (2003) pp. 311-322.
Kojima et al., "*Rhenium containing binary catalysts for ammonia synthesis,*" Applied Catalysis A: General 209 (2001) pp. 317-325.
Kojima et al., "*Cobalt Rhenium Binary Catalyst for Ammonia Synthesis,*" Chemistry Letters 2000 pp. 912-913, The Chemical Society of Japan.
Shustorovich et al., "*Synthesis and decomposition of ammonia on transition metal surfaces: bond-order-conservation-Morse-potential analysis,*" Surface Science Letters, Surface Science Letters 259 (1991) L791-L796, North-Holland, Elsevier Science Publishers B.V.
Asscher et al., "*The Ammonia Synthesis over Rhenium Single-Crystal Catalysts: Kinetics, Structure Sensitivity, and Effect of Potassium and Oxygen,*" Journal of Catalysis 98, pp. 277-287 (1986).

*Primary Examiner* — Thuan D Dang

(57) ABSTRACT

The invention relates to minimizing ammonia poisoning of a catalyst and to a xylene isomerization process using said catalyst.

7 Claims, 4 Drawing Sheets

MANUFACTURING PROCESS

CROSS REFERENCE TO RELATED APPLICATIONS

This application claims priority to and the benefit of Provisional Application No. 61/733,656, filed on Dec. 5, 2012, the disclosure of which is incorporated herein by reference in its entirety.

FIELD OF THE INVENTION

The invention relates to the production of ammonia by a rhenium catalyst, to minimizing ammonia poisoning of said catalyst, and to a xylene isomerization process including a start-up procedure minimizing ammonia production and/or ammonia poisoning by said catalyst.

BACKGROUND OF THE INVENTION

Paraxylene is commercially important because it is a precursor for polyester fibers, films, bottle plastic, and the like. A typical equilibrium mixture of xylene isomers is contains only about 22-24 wt % paraxylene. In a conventional aromatics complex, paraxylene is separated from its C8 aromatic isomers by a process including adsorptive separation or crystallization processes, to produce a paraxylene-enriched stream and a paraxylene-depleted stream ("raffinate"). The raffinate is isomerized to equilibrium and recycled for paraxylene separation.

There are a number of known commercial processes to accomplish the isomerization of raffinate to equilibrium. For instance, there is a process that takes the paraxylene-depleted xylenes stream, which also includes ethylbenzene, and dealkylates ethylbenzene to produce benzene and ethylene, while isomerizing the xylenes to an equilibrium mixed xylene product. The ethylbenzene dealkylation and xylene isomerization reactions can be carried out in a single step or the steps can be decoupled and accomplished step-wise in a dual-bed catalyst system. For illustration of the latter process, see, for instance, U.S. Pat. Nos. 5,004,855; 5,516,956; and 6,028,238.

Rhenium (Re) is used to give metal functionality to certain zeolite-based high activity isomerization catalysts, such as in one or more of the aforementioned prior art. Re gives high olefin saturation activity with minimal aromatic ring saturation in the ethylbenzene dealkylation reaction in the presence of hydrogen. However, it has been discovered that during conventional start-up procedures in a xylenes isomerization process, the rhenium metal-modified catalyst readily catalyzes the ammonia synthesis reaction when nitrogen and hydrogen are present together and in contact with said catalyst, even at at relatively low temperature and pressure, as shown below:

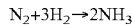

$$N_2 + 3H_2 \rightarrow 2NH_3$$

Ammonia formation occurs over the rhenium promoted xylene isomerization catalyst during the unit start-up, which includes introduction of nitrogen gas to remove oxygen and moisture, followed by the introduction of hydrogen for the purpose inter alia of reducing the metal, while at the same time increasing the temperature of the system to operational temperatures. Thus, the start-up procedure, including catalyst dry-out phase and introduction of hydrogen usually results in a relatively long period with significant nitrogen concentration in hydrogen gas at high temperature and pressure, typically above 180° C. and a pressure above 0.5 MPa. These gases are recycled in typical isomerization systems. In several commercial applications using this catalyst, ammonia was detected in the recycle gas during the catalyst dry-out phase. While ammonia production from hydrogen and nitrogen is per se is generally highly desirable, in the context of zeolite-based xylene isomerization it is not, as ammonia is a poison for the acid sites of the zeolite-based catalyst. Extended exposure results in potentially severe loss of catalyst activity. Since the rhenium promoter inherently provides high activity for ammonia synthesis, it is desirable to minimize the exposure of the rhenium-promoted zeolite xylene isomerization catalyst to ammonia in order to maintain its high performance characteristics.

The present inventors have surprisingly discovered a procedure that decreases the amount of ammonia produced during the catalyst dry-out phase and introduction of hydrogen and minimizes catalyst poisoning by ammonia.

SUMMARY OF THE INVENTION

The invention relates to the production of ammonia by a rhenium catalyst, to minimizing ammonia poisoning of said catalyst, and to a xylene isomerization process including a start-up procedure minimizing ammonia production and/or ammonia poisoning by said catalyst.

It is an object of the invention to provide a start-up procedure that does not require retrofitting or replumbing of existing equipment that can be simply implemented by one of ordinary skill in the art without more than routine experimentation.

It is another object of the invention to provide a catalyst dry-out procedure that minimizes catalyst damage due to the contact of an atmosphere comprising hydrogen and nitrogen gases.

These and other objects, features, and advantages will become apparent as reference is made to the following detailed description, preferred embodiments, examples, and appended claims.

DETAILED DESCRIPTION

Figure 1:
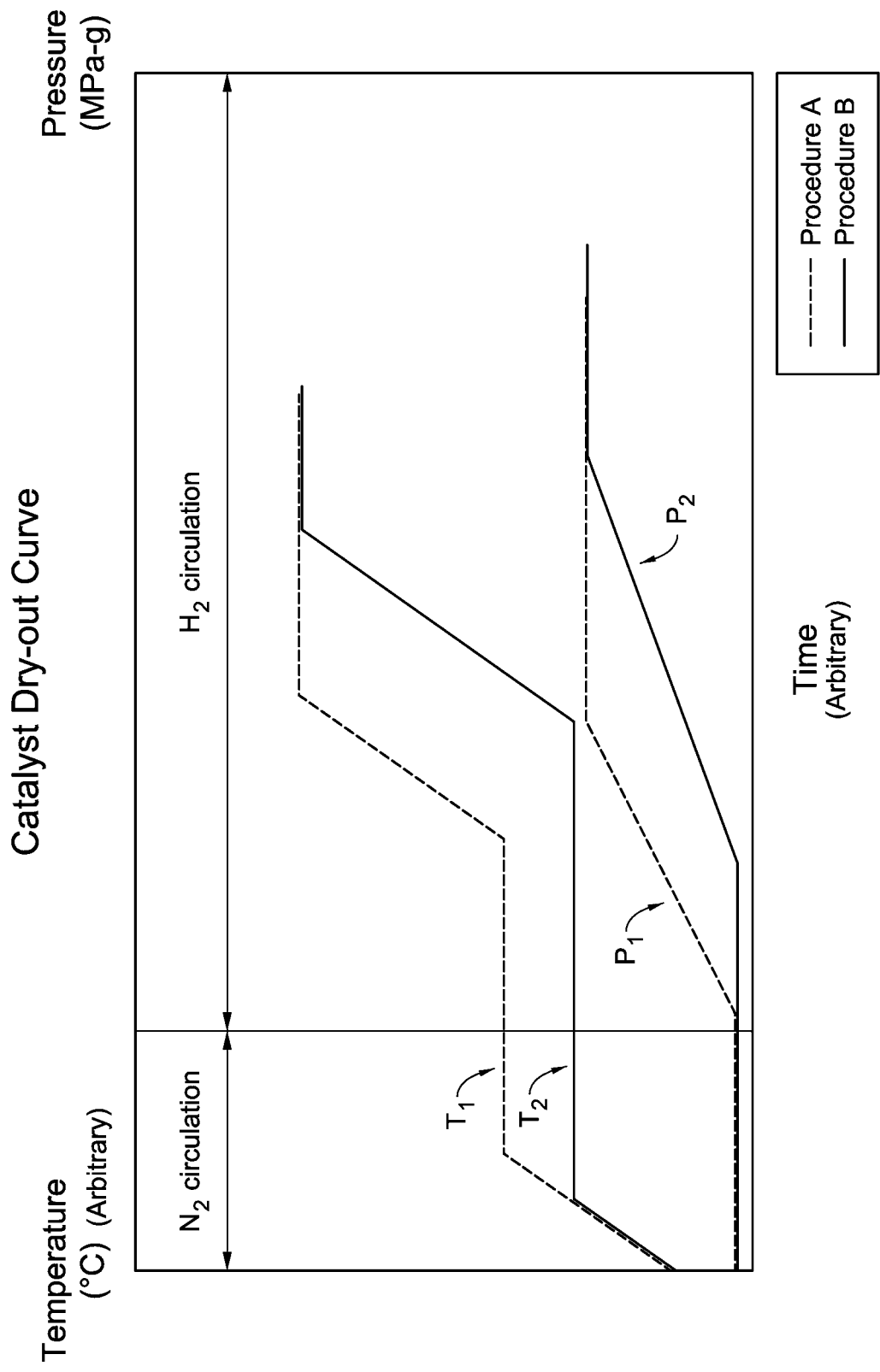
FIG. 1 illustrates an embodiment of a procedure for the catalyst dry-out procedure according to the invention.

According to the invention, in a xylene isomerization unit start-up using a rhenium-based isomerization catalyst, catalyst poisoning is minimized by reducing temperature and pressure during the process start-up procedure.

In an embodiment, the process of the invention comprises contacting nitrogen and hydrogen in the presence of a rhenium-based zeolite at a temperature of below 180° C. and a is pressure of below 0.5 MPa, which may be for a period of time that is predetermined, and/or operator determined or assisted and/or computer determined or assisted, or a combination thereof.

In an embodiment, there is a xylene isomerization unit start-up wherein nitrogen is used initially to purge oxygen from the reactor system. This is also a useful time to conduct leak tests on the equipment. The equipment comprises a reactor system including a xylene isomerization reactor (comprising one or more catalyst beds), a source of mixed xylenes for said isomerization reactor, a high pressure separator to separate liquid products from gaseous products downstream of said isomerization reactor, separation equipment to separate gases produced in the reactor (e.g., ethylene) from the recycled gases (e.g., $N_2$, $H_2$), plus associated furnace(s), valves/vents, heat exchange devices, and other apparatus such as would be apparent to one of skill in the art. Downstream of this equipment would also be separation devices, e.g., fractionators, adsorptive separation devices and/or crystallizers, and so forth, to provide a paraxylene-enriched product stream and a raffinate stream which is returned to the isomerization reactor. The equipment per se does not form a part of the present invention except as otherwise may be specifically pointed out hereinbelow.

After purging of oxygen in the reactor system with nitrogen, hydrogen rich gas is introduced into the reactor system, typically through introduction into the recycle line, and the hydrogen rich gas is used to remove any moisture adsorbed on catalyst and reduce rhenium oxide to activate the catalyst. The system is vented under hydrogen pressure during this period so that nitrogen is purged and replaced by the hydrogen gas. It was surprisingly discovered that when the change-over of atmosphere from nitrogen to hydrogen occurs during the reactor heat-up and pressurization stage in the presence of a rhenium-based zeolite catalyst, an environment for ammonia formation is present. Ammonia can form over the rhenium catalyst in the presence of nitrogen and hydrogen at temperatures as low as 180° C.

In order to mitigate the problems potentially caused by the formation of ammonia in xylene isomerization, so that the rhenium-based zeolite catalyst can have an improved function as a xylene isomerization catalyst, it has been found that ammonia formation is decreased to acceptable levels or eliminated when the aforementioned change-over from nitrogen to hydrogen occurs at lower temperatures, such as below 180° C., or 160° C., or 150° C., and at a pressure such as below 0.5 MPa, such as from atmospheric pressure (101.325 kPa) to 0.5 MPa, or from above atmospheric pressure to 0.50 MPa.

In an embodiment, the temperature is not increased until the nitrogen level in the system has decreased to below 1.0 vol %, such as measured, by way of example, in the recycle gas line, and hydrogen purging of nitrogen continues as the heat-up progresses. Such nitrogen displacement at low temperature and pressure decreases the ammonia synthesis reaction when compared with the traditional start-up processes that occur with higher temperature and pressures. It will be understood that either one of (i) low temperature, or (ii) low pressure, will decrease ammonia production, however, not as well as simultaneously doing both (i) and (ii). It will further be understood that the measurements discussed herein, such as nitrogen levels, ammonia levels, moisture levels, and so on, can be measured at various places in the reactor system, as would be readily understood by one of ordinary skill in the art in possession of the present disclosure, and are conveniently measured for instance in the gas recycle line of the reactor system described elsewhere herein. Reactor temperatures and pressures, of course, are best taken from the reactor itself, such as at the inlet or outlet of said reactor and/or at the top and/or bottom of the bed. If there is more than one temperature and/or pressure measurement in said reactor, then the reported temperature would be an average value of all measurements.

Thus, in an embodiment, nitrogen purge of oxygen occurs in a first procedure at the conditions of $T_1$ and $P_1$ and then hydrogen purge of nitrogen occurs in a second procedure at conditions of $T_2$ and $P_2$, wherein $T_1 \geq T_2$ and $P_1 \geq P_2$. In a preferred embodiment the change over from $T_1$ to $T_2$ occurs before the introduction of hydrogen and at the point of introduction of hydrogen the change over from $P_1$ to $P_2$ is commenced. By lowering the temperature and pressure before or during the change over from nitrogen to hydrogen, ammonia production is decreased. Maximizing the timing of attenuation of temperature and/or pressure relative to the timing of introduction of hydrogen gas, and the flow rate thereof, is within the skill of the artisan in possession of the present disclosure.

The invention may be better understood by reference to the following experiments and figures, which are intended to be representative of and not limiting of the present invention. One of ordinary skill in the art will realize that the invention may be practices other than as specifically disclosed herein.

FIG. 1 illustrates an embodiment of the procedure just discussed above. FIG. 1 illustrates a first procedure (dotted line, Procedure A) at the conditions of $T_1$ and $P_1$ and a second procedure (solid line, Procedure B) at conditions of $T_2$ and $P_2$, wherein $T_1 \geq T_2$ and $P_1 \geq P_2$ and wherein the solid vertical line in the middle of the graph at the junction of $N_2$ circulation and $H_2$ circulation is the point at which $H_2$ is introduced while the $N_2$ input is stopped. At the introduction of $H_2$, when both $H_2$ and $N_2$ are present in contact with the catalyst, ammonia is produced. By altering the temperature and pressure conditions under is which contact of $H_2$ and $N_2$ contact the catalyst, ammonia production is attenuated. By lowering the temperature and pressure, as illustrated in FIG. 1, it has been found that ammonia production is decreased. In contrast, by raising temperature and pressure, e.g., in the case of $T_2 > T_1$ and $P_2 > P_1$ (not shown), it has been found that ammonia production is increased and further it has been found that such an increase causes negative effects on the catalyst and on the isomerization of xylenes. Attenuating only temperature or only pressure causes less of an effect. Again, maximizing the timing of attenuation of temperature and/or pressure relative to the timing of introduction of hydrogen gas, and the flow rate thereof, is within the skill of the artisan in possession of the present disclosure.

In another embodiment of the invention, there is a process which includes the use of "depressure/repressure" cycles to purge any ammonia formed from the reactor system. Nitrogen is introduced in the reactor system, such as via a recycle line gas compressor, to remove any trace amount of oxygen, as previously mentioned. When hydrogen is subsequently introduced and circulated in the reactor system, it is difficult if not impossible to remove all of the nitrogen from the system. Without wishing to be bound by theory, using the assumption that some level of ammonia formation is inevitable, the present inventors have found that, in embodiments, the use of "depressure/repressure" cycles is an effective way to purge both ammonia and moisture from the system during the dry-out period in the xylene isomerization process. The depressure cycle should go to as low a pressure as possible, while allowing for stable recycle gas compressor operation.

Figure 2:
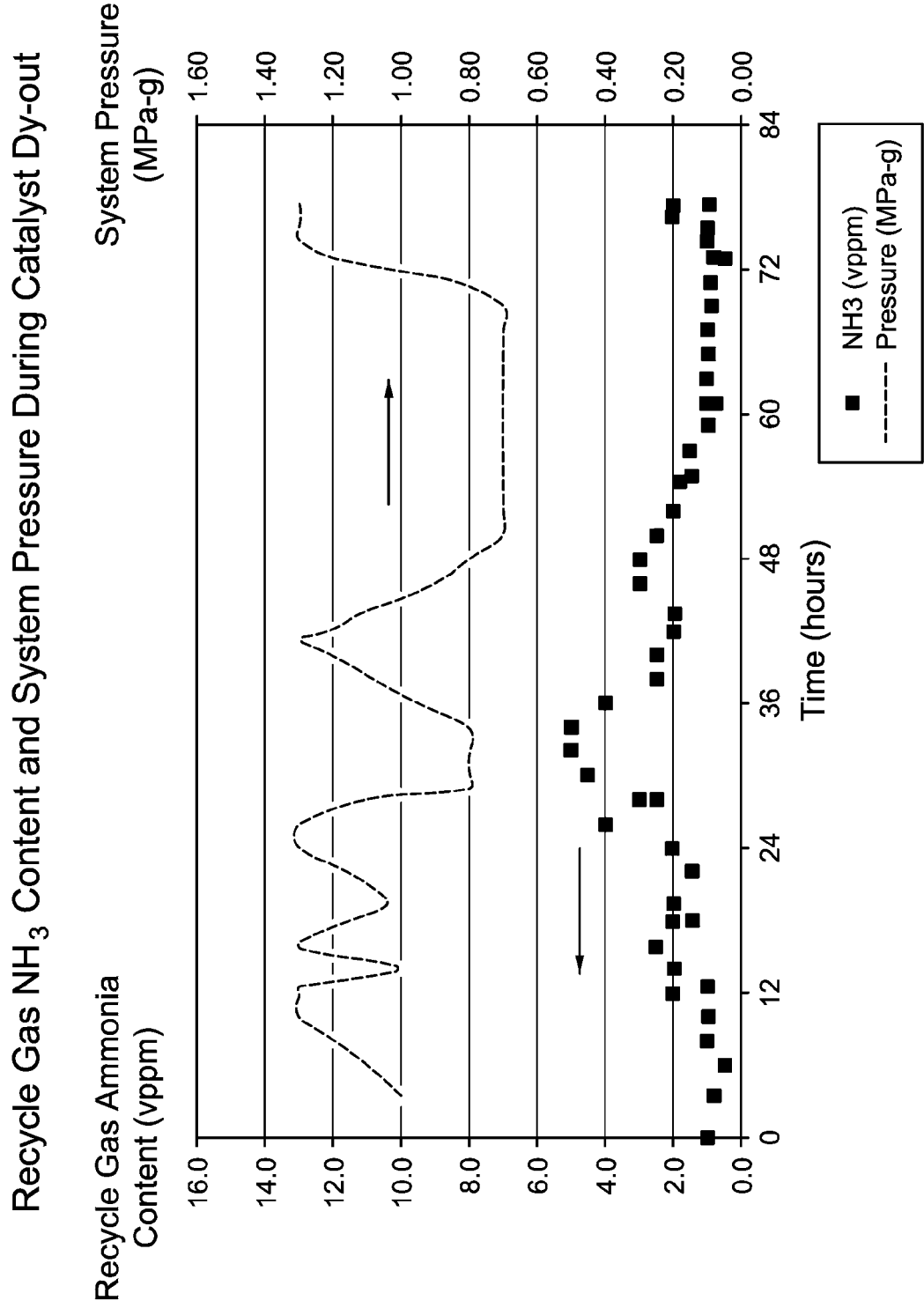
FIG. 2 illustrates results for an embodiment of the invention.

The "depressure/repressure" embodiment is illustrated by the example shown in FIG. 2. In FIG. 2, the left side of the y-axis is the measurement of ammonia in the recycle line during the catalyst dry-out procedure of the present invention; the right side is the total system pressure. As illustrated in the embodiment shown in FIG. 2, which is just one of any number of possible "depressure/repressure" scenarios, during a first period of time during introduction of hydrogen gas, the ammonia content (as measured conveniently in the recycle line) increases (illustrated by the black boxes at the bottom of the graph), as the system pressure builds up (dashed pressure line, as measure on the right side of graph). The system is then vented or "depressured" and accordingly pressure in system decreases, and ammonia presence, again measure in the recycle line, decreases. The venting is stopped and the system is "repressured" in the same manner. This process of "depressure/repressure" is continued until the ammonia level is minimized.

In addition to minimize the exposure to ammonia during the catalyst dry-out preceding the xylene isomerization process, it may be necessary to accept a recycle gas is moisture level above target, e.g., 200 vppm. Experience from several start-ups showed that final dry-out step resulted in a moisture level of 500 vppm without sacrificing catalyst performance. FIG. 2 is further discussed in detail, below.

After the catalyst dry-out according to the present invention, the system can then commence xylene isomerization by introduction of the paraxylene-depleted feedstream or raffinate to contact the catalyst.

The catalyst is a rhenium-based zeolite catalyst suitable for isomerization of a paraxylene-depleted aromatic hydrocarbon stream (having paraxylene in the amount of, for instance, from 0 wt % to 15 wt %, such as from about 0.1 wt % to about 2.0 wt % or from about 10 wt % to about 12 wt %, and the like) to equilibrium or near-equilibrium, e.g., to in the range of 22-24 wt %. Other metals may be present, such as Pt, Fe, Ru, i.e., the traditional "Group VIII" metals (now Groups 8-10 of the Periodic Table). The zeolite may be selected from at least one of the MFI, MTW, and MOR family of zeolites, and mixtures thereof. The preparation of the metal-containing catalyst does not per se form a part of the present invention but rather is within the skill of the person having ordinary skill in this art based on prior art preparations. An example of such catalyst preparation can be found in U.S. Pat. No. 5,990,365.

Successful testing in commercial-scale units demonstrate improved xylene isomerization process operation. During recent unit start-ups, short-term ammonia levels as high as 5 vppm were observed during the dry-out phase, and these units still appear to be providing excellent performance. Accordingly, in embodiments, a target of no more than 5 vppm is targeted for the rhenium promoted xylene isomerization catalyst start-ups.

The following additional description of FIG. 2, also intended to be representative and not limiting of the present invention, follows from an actual example.

In the start-up of an isomerization unit of the commercial type per se known in the art, the unit leak check and flange hot-bolting were completed at 100° C. The reaction section environment was switched from nitrogen to hydrogen at this temperature. The unit was maintained under a slightly positive pressure (<0.1 MPa) during $N_2$ displacement. The reactor temperature was not increased until the nitrogen level decreased to below 4 vol %, and gas purging continued as the heat-up progressed.

The presence of ammonia in the recycle gas was first detected at a reactor temperature of 220° C. The analysis of the recycle gas showed 1 vppm $NH_3$ while the corresponding make-up gas sample showed no ammonia present. This suggests that the ammonia was being formed from nitrogen and hydrogen in the presence of the rhenium is catalyst. The nitrogen was coming from two sources: (1) nitrogen remaining in the system following the purging step (analysis showed 1.88 vol % $N_2$), and (2) nitrogen entering the system with the make-up gas (analysis showed typical $N_2$ content of 200 vppm). To mitigate the effect of ammonia on the catalyst, the make-up gas rate into the recycle line was increased by 50% to increase the rate of moisture removal and to purge the formed ammonia from the system. The "depressure/repressure" cycles, discussed above, were also used to purge the recycle gas. As shown in FIG. 2, the reactor pressure during the depressure/repressure cycle varied from about 0.7 to about 1.3 MPa-g, periodically. The depressuring steps released the ammonia absorbed in the catalyst pores, which allowed for the ammonia to be purged. When the reactor pressure decreased from about 1.3 to about 0.8 MPa-g, the ammonia concentration in the recycle gas increased from about 2 to about 5 vppm. During the course of dry-out process, ammonia desorbed from the catalyst was gradually purged out, thus, ammonia concentration in the recycle gas decreased over the time. The recycle gas contained from 0-5 vppm $NH_3$, averaging 2 vppm. The catalyst exposure was relatively brief and at reduced temperature, both of which should reduce the potential for any catalyst activity damage.

Additionally, when the catalyst dry-out and reduction were completed, the reactor temperature was ramped to oil-in temperature of 360° C. At this hold point, both ammonia and moisture level in the recycle gas increased due to increased rates of reaction and desorption. To minimize further exposure to ammonia, a higher level of moisture (500 vppm) than the normal target (200 vppm) was accepted—meaning the dry-out period was substantially decreased—and hydrocarbon feed introduction immediately followed.

Catalyst performance following the start-up using the above method when compared with the prior art method can be shown by a comparison of FIGS. 3 and 4, as discussed below.

Figure 3:
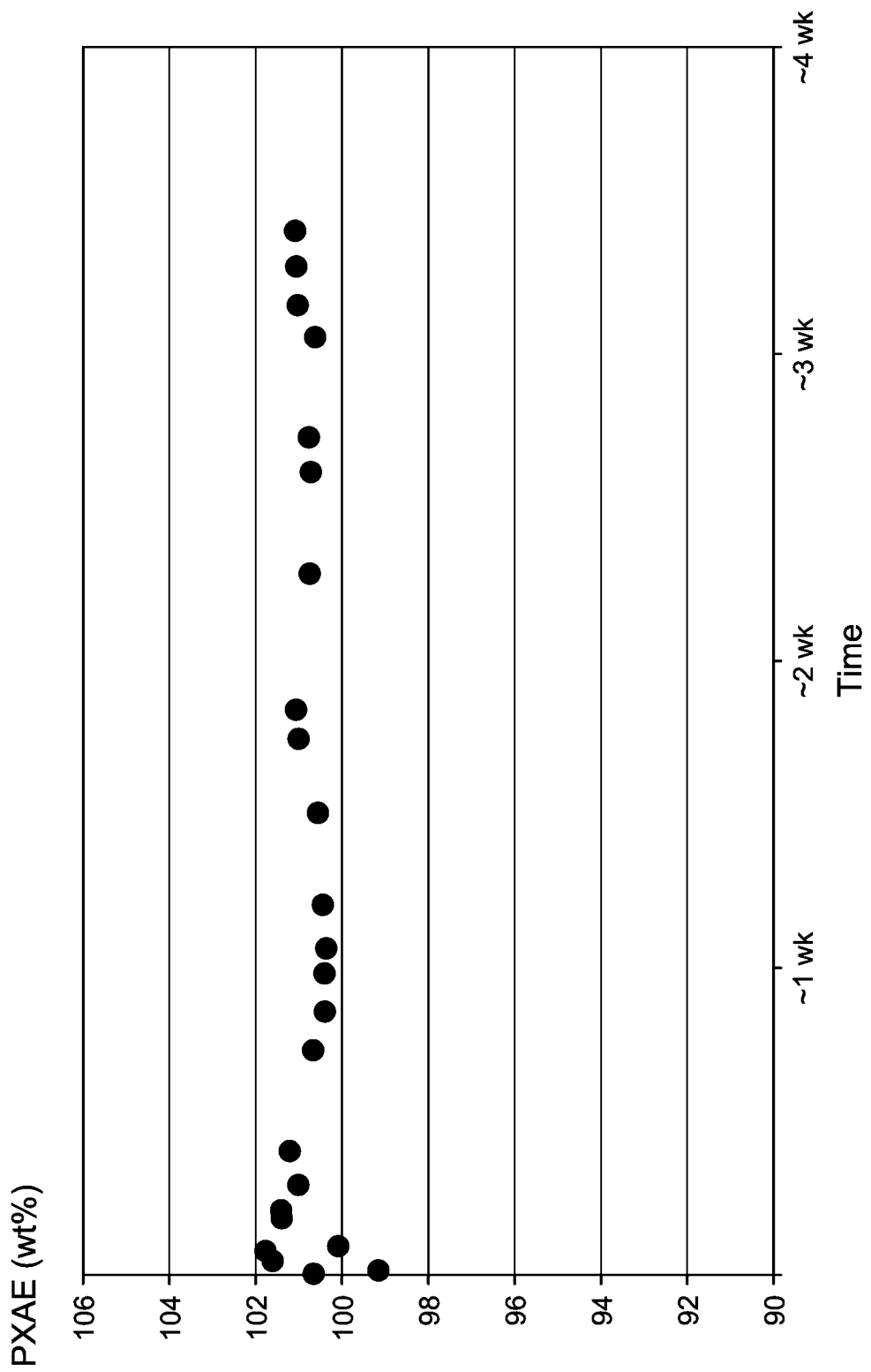
FIGS. 3 and 4 provide a comparison of the present invention versus conventional start-up procedures using indicia of approach to paraxylene equilibrium (PXAE).

The paraxylene (PX) Approach to Equilibrium ("PXAE"), a measure of the catalyst's ability to isomerize xylenes, has averaged 100.8% since the unit start-up, as shown in FIG. 3. The reason the average can be about 100% is because of the following. PXAE is calculated as follows: PXAE=100*([PX(product)−PX(feed)]/[PX(theoretical at equilibrium)−PX(feed)]). PX(theoretical at equilibrium) values were taken from *The Chemical Thermodynamics of Organic Compounds*, Stull, Westrum and Sinke, published by John Wiley & Sons, which lists a series of theoretical PX % in mixed xylenes as a function of temperature, such PX % values being all lower than 24%. Since these are theoretical values, it is possible for PXAE to be greater than 100%. What is important is not the absolute value arrived at, but the comparison of one PXAE value to another PXAE value, provided, as is the case herein, the same consistent calculation method is used.

Figure 4:
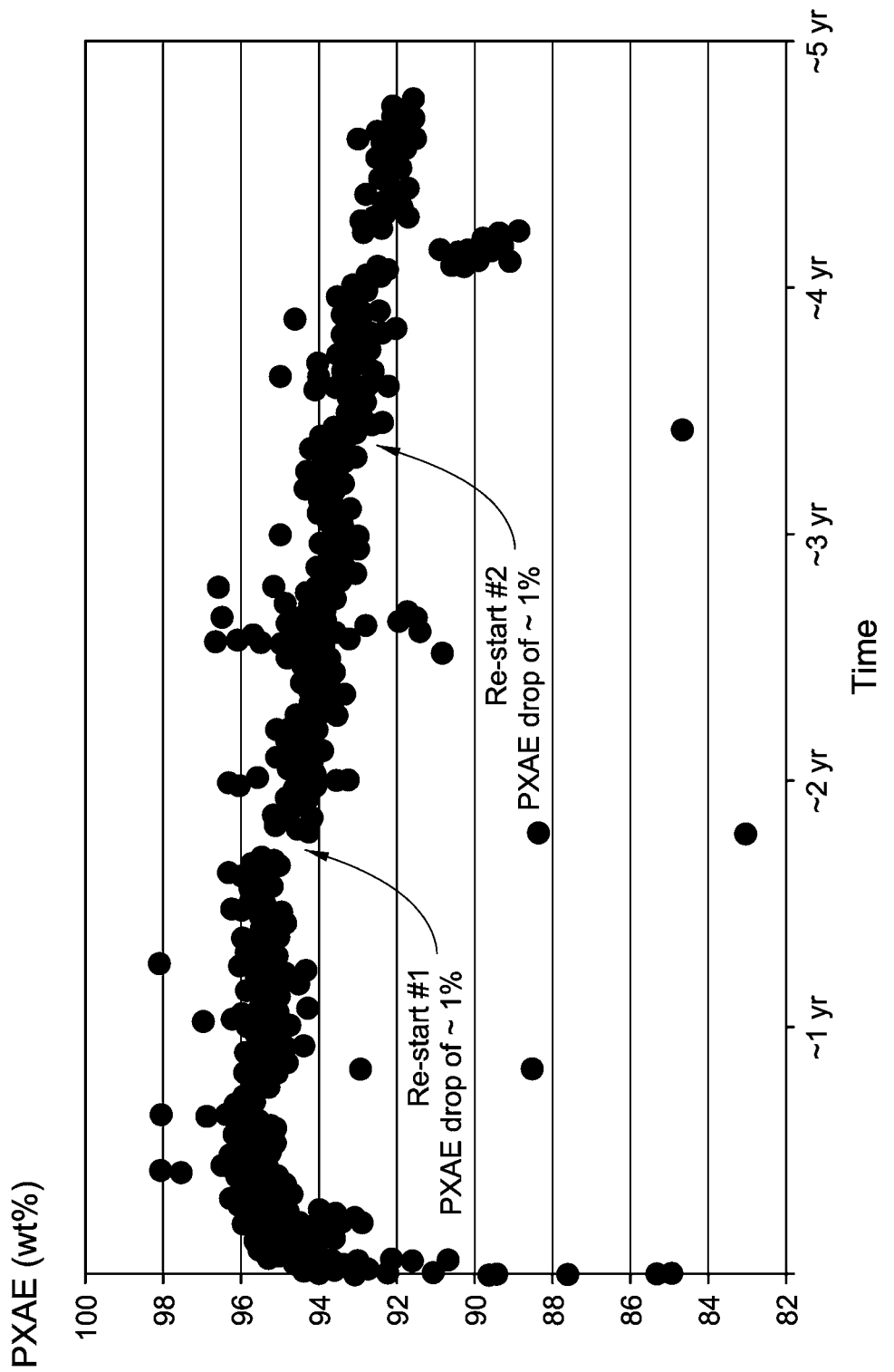

Catalyst performance in the same unit, following the start-up, but without using the above method is shown in FIG. 4. As can be seen, the PX Approach to Equilibrium (PXAE) is substantially lower in average (approximately 96%) than the average PXAE (100.8%) shown in FIG. 4. In the absence of the use of the above described procedure during dry-out, but rather following the conventional start-up (or restart) procedures described herein, the catalyst bed has been substantially exposed to ammonia and its isomerization function poisoned by ammonia, thus the substantially lower PXAE value after start-up. Following a cycle of operation during which PXAE averaged 95-96% throughout said cycle, the unit was shut-down and then restarted (Restart #1). PXAE decreased by a full 1% on restart due to additional exposure to ammonia during the dry-out procedure, other operating conditions being the same as prior to shutdown. PXAE averaged 94% during the second cycle, until a new shutdown occurred. Once again on restart (Restart #2) PXAE decreased by a full 1% due to additional exposure to ammonia during the dry-out procedure, other operating conditions being the same as prior to shutdown.

While other factors (e.g., higher WHSV) contributed to PXAE being lower at the start of cycle in FIG. 4 (approximately 96%) than in FIG. 3 (100.8%), it is believed that lower ammonia formation due to the start-up procedure of the present invention is believed to be at least one of the contributing factors to said lower PXAE.

The invention has been described above with reference to numerous embodiments and specific examples. Many variations will suggest themselves to those skilled in this art in light of the above detailed description. All such obvious variations are within the full intended scope of the appended claims. Trade names used herein are indicated by a™ symbol or ® symbol, indicating that the names may be protected by certain trademark rights, e.g., they may be registered trademarks in various jurisdictions. All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted. When numerical lower limits and numerical upper limits are listed herein, ranges from any lower limit to any upper limit are contemplated.

What is claimed is:

1. A process in a reactor system comprising a reactor having a rhenium-based MFI zeolite catalyst therein, said process comprising:
   (i) a step comprising introducing nitrogen gas into said reactor system to at least partially displace any oxygen and/or moisture in said reactor system under conditions including a temperature T1 and a pressure P1, and then contacting said rhenium-based MFI zeolite catalyst with said nitrogen gas for a predetermined period of time and/or until oxygen and/or moisture in said reactor system fall to a predetermined level;
   (ii) a step comprising introducing hydrogen gas into said reactor system to at least partially displace said nitrogen in said reactor system under conditions including a temperature T2 and a pressure P2, and then contacting said rhenium-based MFI zeolite catalyst with said hydrogen gas for a period of time which may be predetermined and/or measured by one or more of reactor system characteristics selected from ammonia levels, oxygen levels, moisture levels, and nitrogen gas levels measured in said reactor system;
   wherein said conditions include T2<180° C.<T1 and P2<0.5 MPa<P1; and
   (iii) a step comprising contacting said rhenium-based MFI zeolite catalyst with a paraxylene-depleted feedstream comprising orthoxylene and metaxylene, whereby at least a portion of said orthoxylene and metaxylene are isomerized to paraxylene.

2. The process of claim 1, further comprising, after step (ii) and before step (iii), at least one step (a), comprising increasing said reactor system pressure by increasing the pressure of hydrogen gas in said reactor system, followed by venting of said reactor system to decrease said reactor system pressure.

3. The process of claim 1, wherein hydrogen is introduced into said reactor to displace nitrogen at a temperature less than T1 and a pressure less than P1 for a period of time until at least one of the following conditions is measured in said reactor system: (i) ammonia levels are at or below a predetermined level; and (ii) nitrogen levels are at or below 1.0 vol %, based on the volume of total gases.

4. The process of claim 1, wherein T2≤160° C.

5. The process of claim 1, wherein at least one of the following conditions is measured during the contacting of step (ii) before beginning step (iii): (aa) the moisture level as measured in the recycle gas line is less than 500 vppm; (bb) nitrogen level as measured in the recycle gas line has decreased to below 1.0 vol %; (cc) ammonia level as measured in the recycle gas line is at or below 5 vppm.

6. The process of claim 5, wherein at least two of said conditions are measured during said contacting of step (ii) before beginning step (iii).

7. The process of claim 5, wherein all of said conditions are measured during said contacting of step (ii) before beginning step (iii).

* * * * *